United States Patent [19]
Schindel et al.

[11] Patent Number: 5,287,331
[45] Date of Patent: Feb. 15, 1994

[54] AIR COUPLED ULTRASONIC TRANSDUCER

[75] Inventors: David W. Schindel, Kingston, Canada; David A. Hutchins, Kenilworth, England

[73] Assignee: Queen's University, Kingston, Canada

[21] Appl. No.: 966,649

[22] Filed: Oct. 26, 1992

[51] Int. Cl.⁵ ............................................. H04R 17/00
[52] U.S. Cl. ..................................... 367/140; 29/25.35
[58] Field of Search ............... 367/157, 170, 180, 140; 310/326, 334, 337, 309; 29/25.35, 594

[56] References Cited

U.S. PATENT DOCUMENTS

| | | | |
|---|---|---|---|
| 4,381,672 | 5/1983 | O'Connor et al. | 310/309 |
| 4,672,591 | 6/1987 | Breimesser et al. | 367/157 |
| 5,153,859 | 10/1992 | Chatigny et al. | 367/157 |

Primary Examiner—Daniel T. Pihulic
Attorney, Agent, or Firm—Richard J. Hicks

[57] ABSTRACT

An acoustic transducer which is operable in air up to at least 2MHz is described. A conducting substrate, usually a silicon wafer is etched to provide a selected pattern of micro pits up to about 30 μm or more deep. A dielectric film, such as a polyimide film is placed over the etched surface so as to trap air in each individual pit. A conducting upper layer is then superimposed over the dielectric film. When a potential is applied between the substrate and the upper layer the upper layer is driven into motion and enhanced by the vibrations of the air pockets. Alternatively a smooth substrate may be employed in conjunction with an etched dielectric film to achieve the same result. These transducers are useful for non-destructive testing of large structures or for medical diagnostic and therapeutic purposes, without the need for a liquid or gel coupling agent.

23 Claims, 1 Drawing Sheet

AIR COUPLED ULTRASONIC TRANSDUCER

FIELD OF INVENTION

This invention relates to a generator and detector of ultrasound in air at frequencies from audio to in excess of 600 kHz. More particularly this invention relates to an air coupled acoustic transducer which operates as a source and receiver up to at least 2 MHz.

BACKGROUND OF INVENTION

Electrostatic transducers for generating and detecting sound waves are well known in the art and attention is directed to U.S. Pat. Nos. 3,544,733; 3,946,422; 3,961,291; 4,329,547; 4,419,545; 4,908,805; 4,429,193; 4,439,642; 4,885,781; 4,993,072; 5,101,543; 4,809,355; 4,594,897; 4,85,783; 4,558,184 and 4,593,567, which are typical of known devices and which generally include a moveable conductive material in juxtaposition to a moveable non-conductive dielectric material, both of which vibrate in unison. In most instances a conductive backplate in the form of a plate or foil is spaced from the dielectric material which is usually a thin film of plastic such as a Mylar film. Between the two there is an air gap or space of predetermined thickness. The size and thickness of the air gap is critical and many attempts have been made to vary this gap by the use of multi dielectric layers, and spaces of varying types. The problem is that ultrasound is highly attenuative in air above about 600 kHz and conventional ultrasonic devices cannot adequately couple vibrational energy from solid to gas due to the large impedance mismatch. Use of conventional transducers for such applications as non-destructive testing of large planar planar surfaces is greatly hampered by the need to use an external coupling agent such as a gel. Many prior art patents rely on a simple air pocket between the dielectric material and the backing electrode so that the dielectric does not touch the backing electrode. Others, such as U.S. Pat. No. 4,908,805, support the dielectric membrane covering the backing electrode on posts and use glue to hold the membrane in place, and then provide openings in the backplate. They are designed for use at relatively low frequencies and the space taken up by the glue is effectively wasted space that could be used for generation of ultrasonic energy. U.S. Pat. No. 4,419,545 provides means for varying the area of the open holes in the backplate leading to the single air pocket in order to affect the frequency response and sensitivity but the vibrating element does not touch the back plate.

There is, therefore a need for improved acoustic transducers which can operate efficiently at frequencies up to at least 2 MHz, and it is believed that this can be attained by careful control of the surface roughness of the backplate so as to provide a plurality of air pockets each of which vibrates. Such transducers would find applications testing large surfaces for internal flaws, among other applications obvious to those skilled in the art. Such other applications include human diagnostic and therapeutic uses. As is well known ultrasound, using a gel coupling agent, is used extensively for medical purposes.

OBJECT OF INVENTION

An object of the present invention is to provide efficient acoustic transducers which can operate in air up to frequencies of at least 2 MHz, thereby eliminating the need for coupling liquids, gels or the like.

BRIEF STATEMENT OF INVENTION

By one aspect of this invention there is provided an acoustic transducer operable in air up to at least 2 MHz, comprising: a substrate having at least one conducting surface and having a plurality of pits of selected size and shape distributed in a selected pattern over at least one surface thereof;
at least one planar dielectric film superimposed over said substrate so as to provide a plurality of air pockets between said substrate and said dielectric film; and
a planar conducting upper electrode superimposed on said dielectric film.

By another aspect of this invention, there is provided an acoustic transducer operable in air up to at least 2 MHz, comprising a substrate having at least one conducting surface;
at least one dielectric film, having a plurality of pits of selected size and shape distributed thereover in a selected pattern, superimposed over said substrate so as to provide a plurality of air pockets between said substrate and said dielectric film; and
a conducting upper electrode superimposed on said dielectric film.

By yet another aspect of this invention there is provided a method for producing an acoustic transducer operable in air up to at least 2 MHz, comprising:
(a) producing a selected pattern of pits in a planar surface of a conducting substrate;
(b) superimposing said pitted surface with a film of dielectric material so as to trap air into a plurality of said pits; and
(c) superimposing a planar conducting electrode over said dielectric film.

DETAILED DESCRIPTION OF PREFERRED EMBODIMENTS

Figure 1:
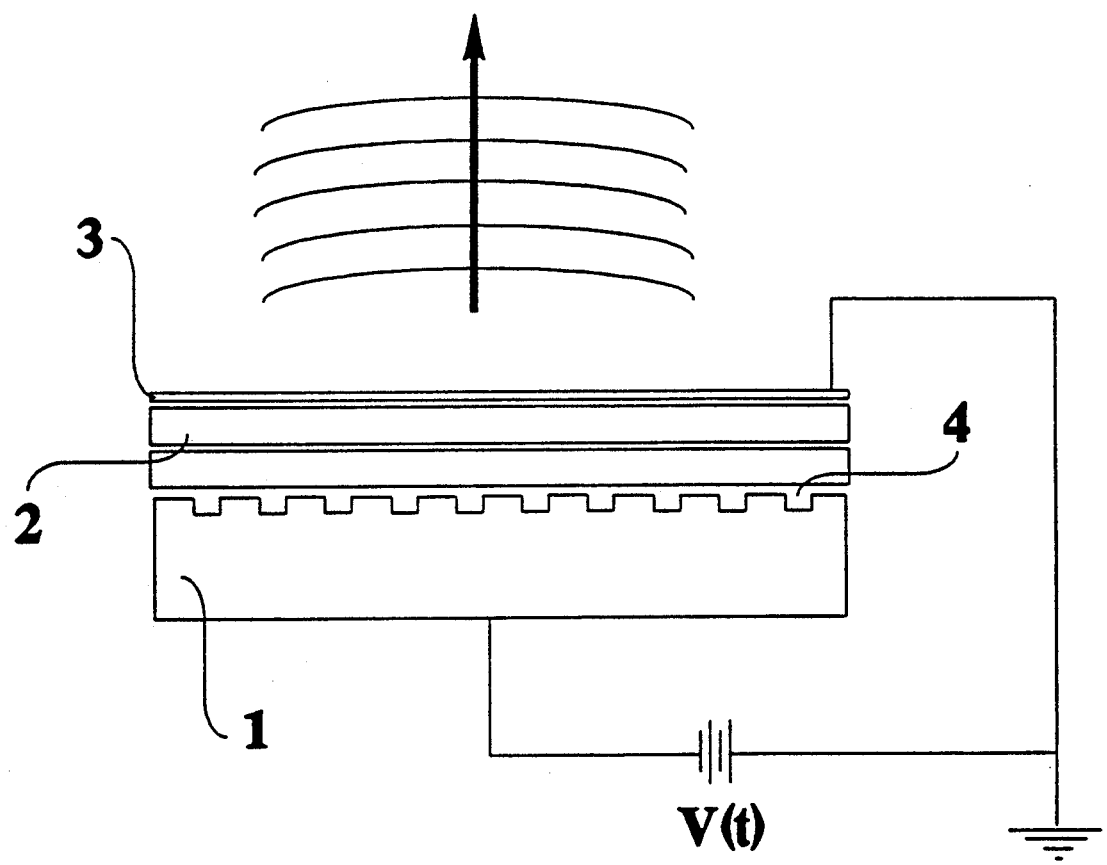
FIG. 1 is a schematic cross sectional view of one embodiment of the present invention.

Commercially available ultrasound devices for use beyond about 600 kHz generally rely upon using solid piezoelectric elements, which may be embedded in a polymer matrix, which is formed in the shape of a thin disk. Electrodes are placed on each side of the disc so that an electric field can be applied to the piezoelectric elements and excite them into vibration. The polymer matrix serves both to decrease the acoustic impedance from that of a solid and to dampen the vibrations of the inherently resonant elements. In order to transfer a measurable degree of acoustic energy to the air, it is usually necessary that one side of the disc be loaded only by air (a so-called air backed transducer) while applying a thin impedance matching layer to the other face (a so-called ¼ wave matching layer). Such devices are capable of reaching operational frequencies of about 5 MHz, but their sensitivities are low, and they are often resonant devices in order to get useable output, which means that they can only be operated at a single well defined frequency of design.

In contrast the capacitance devices of the present invention have an order of magnitude greater sensitivity in detection and generation than the piezoelectric air-coupled transducers described above. This means that in any practical ultrasonic system two orders of magnitude greater sensitivity result as a source and a receiver are necessary and the effects are cumulative. Furthermore, as the devices of the present invention are not resonant devices they can be run at any frequency up to and including the bandwidth limit.

As can be seen from FIG. 1, the devices of the present invention are an extension of sonic devices known as electrostatic speakers and microphones which comprise three basic components: namely a rigid conducting backplate 1, preferably planar, a thin dielectric layer 2 superimposed thereon and a thin conducting upper electrode 3. The rigid backplate 1 is provided with random surface contours 4 on one side produced by, for example, roughening with sandpaper. The surface contours serve to introduce air pockets between backplate 1 and the dielectric layer 2. The dielectric layer allows electrical isolation between backplate 1 and upper electrode 3. When a voltage is applied across the backplate and upper electrode an electromagnetic pressure results at the upper electrode 3 which drives it into motion. This motion is tailored and enhanced by the vibrations of the air pockets trapped beneath the dielectric layer 2 in the surface contours 4 of the backplate 1. In most microphones the dielectric layer 2 is a metalized electret such as a Mylar ®, Kapton ® or Teflon ® film which markedly increases the signal strength due to charging processes associated with electret materials. Commercial microphones based on the above construction operate at frequencies up to about 200 KHz. Commercial range finders also exist which can generate frequencies of similar magnitudes.

By carefully controlling the roughness of the backplate 1 by using selected grades of sandpaper and selecting the dielectric layer 2 and upper electrodes from metallized, electret, polymer films it is possible to raise the frequency response to 600-800 KHz with small resonant responses as high as 1.5 MHz. It does not, however, appear possible to raise frequencies higher by these techniques because above about 600 kHz the emergent ultrasonic beam breaks up into many smaller beams, leaving the transducer uncharacterizable. Without wishing to be bound by this theory, it is believed that this is a function of the irregular and non-uniform nature of the roughening process used to create the air pockets in the backplate 1 and variations in the dielectric properties. That is to say, the varied size, distribution, and shape of the air pockets causes the frequency response and sensitivity to vary across the face of the device. Since the air pockets are so small it is believed that conventional mechanical production of the surface contours on the backplate 1 is unlikely to produce the uniformity necessary to produce well characterized capacitive transducers at MHz frequencies.

It is believed that the necessary uniformity can be achieved by employing integrated circuit (IC) techniques in the production of the backplate. Anisotropic etching of a glass, silicon or semi conductor substrate can be effected so as to provide very uniform air pockets having dimensions in the range of microns to tens of microns both deep and wide. Silicon wafers are particularly suitable substrates as they are readily available in thicknesses between about 25μ and 500 μm, are readily etchable by standard techniques and their purity and "perfect" crystalline properties will allow the necessary uniformities.

The dielectric film or films (preferably Mylar ® or Kapton ® but also including piezoelectric polymer films) may be adhered to the etched silicon wafer by any conventional means which may include heat and usually without the need for an adhesive. The dielectric films may also be spun cast onto the substrate from solution in known manner. The spin casting technique is particularly suitable for use with polyimide films.

A metallic upper electrode may be deposited on the surface of the dielectric film by vapour phase deposition or other conventional techniques, such as sputtering.

Alternatively, it may be possible to use a substantially smooth backplate and provide an etched polyimide or other dielectric film.

It will be appreciated that for certain applications the depth of the etch pits in either the substrate or the dielectric film, as the case may be, may extend completely through the substrate or film.

EXAMPLE 1

Preparation of Silicon Backplates by Anistropic Etching

250 μm thick silicon wafers having masking layers of $Si_3N_4$ (~100 Å) and $Si)_2$(~80 Å) were obtained from Virginia Semi Conductor Inc., Fredericksburg, Va. A photoresist layer (Microposit Developer Concentrate Shipley FK059-021085 sold by Shipley Company, Marlboro Mass.) was poured onto the surface of the masked silicon wafers and spun at 3,500 rpm for 60 seconds. The coated wafers were then baked at 90° C. for 30 minutes. A mask comprising a piece of glass with a metallic coating from which an array of 40 μm diameter circles at 80 μm between centres had been removed, and manufactured by Precision Photomask, was placed over the baked photoresist. The baked photoresist and mask were then exposed to UV light of intensity 1.5 $mW/cm^2$ for at least 11 minutes, and developed in a 1:1 solution of Microposit Developer Concentrate Shipley FK059-021085. (Shipley Company) for 25-30 seconds, to remove the exposed circles of the photoresist and reveal an array of $SiO_2$ circles surrounded by photoresist.

The developed wafers were then baked at 135° C. for 30 minutes and the exposed $SiO_2$ circles were etched using buffer HF (10 volume $NH_4$ and 1 volume HF). The $Si_3N_4$ circles were then etched using refluxed boiling 85% phosphoric acid at 170° for about 30 minutes. This revealed an exposed array of bare silicon circles which were then etched using aqueous 44% KOH for 50 minutes. The KOH etchant is an anisotropic etchant for silicon producing pits hexagonal in shape at the surface and up to about 30 μm deep. After chemical etching, residual photoresist was removed by boiling in concentrated $H_2SO_4$ or by immersion in Shipley 1165 photoresist remover for 3 minutes.

At this stage a 1000 Å thick gold film was evaporated onto the side of the wafer containing the pits to provide one electrode of the capacitor. It will, of course, be appreciated that heavily doped or selectively doped silicon wafers could equally well be employed for affecting etching or to provide electrode arrays or potential aperturing and, using similar standard etching techniques, backing plates with selectively arranged pits can be produced.

EXAMPLE 2

Preparation of Dielectric Layer and Upper Electrode

Premetallized thin dielectric films are commercially available. Particularly suitable for the purposes of the present invention are 5 μm Kapton and Mylar films having a thin (~100-1000 Å) aluminum layer evaporated on one surface thereof. An etched backplate produced as in Example 1 and a Kapton film were cleaned by blowing with compressed air to remove dust. The film was then superimposed on the etched surface of the wafer while applying a voltage of about 50 V across the backplate and upper electrode to help eliminate some of the trapped air by sucking the film tightly against the backplate. In conjunction with the applied voltage, gentle rubbing of the surface of the upper electrode with a soft tissue may be effected to remove excess trapped air. Once in place the film is held in place by mechanical means such as to prevent subsequent reintroduction of air into the planar area between film and backplate.

EXAMPLE 3

Preparation of Dielectric layer and Upper Electrode by I.C. Processing

An etched silicon wafer was prepared as in Example 1. A diluted adhesion promoter (QZ3289 and QZ3290—Ciba Giegy) was spun on the surface at 5000 rpm for 30 seconds. A 3 μm polyimide film (Probimide 200 from Ciba-Geigy) was spun onto the prepared surface at 3700 rpm for 50 seconds, and then baked at 89° C. for 30 minutes, plus 150° C. for 15 minutes and 240° C. for 15 minutes. A final high temperature cure at 300° C.–400° C. for 1 hour minutes can be applied to cross link the polyimide. Once the film had been cured a metal electrode, such as aluminum or gold, was deposited on the surface by vapour phase deposition to a thickness between 500–2000 Å; preferably 1000 Å.

It will be appreciated that while this invention has been described with particular reference to operating in air, the devices of this invention can also be operated in a liquid such as water. In such a case it is preferred that an additional thin plastic film be provided over the upper electrode so as to prevent oxidation. Devices operating in water provide a simple means for producing a standard ultrasonic transducer having a well characterized beam profile for calibrating other devices such as piezoelectric tranducers.

We claim:

1. An acoustic transducer operable in air up to at least 2 MHz, comprising: a substrate having at least one conducting surface and having a plurality of pits of selected size and shape distributed in a selected pattern over at least one surface thereof;
   at least one dielectric film superimposed over said pits in said one surface of said substrate so as to provide a plurality of air pockets between said substrate and said dielectric film; and
   a conducting upper electrode superimposed on said dielectric film.

2. An acoustic transducer as claimed in claim 1 including means to secure said dielectric film in superimposed relation on said substrate.

3. An acoustic transducer as claimed in claim 2 wherein said conducting upper electrode comprises a metallic film deposited on said dielectric film.

4. An acoustic transducer as claimed in claim 1 wherein said conducting substrate comprises a semi conducting material.

5. An acoustic transducer as claimed in claim 1 wherein said conducting substrate comprises a glass plate having a conducting surface.

6. An acoustic transducer as claimed in claim 1 wherein said substrate, dielectric film and upper electrode are planar.

7. An acoustic transducer as claimed in claim 4 wherein said semi conducting material is a silicon wafer.

8. An acoustic transducer as claimed in claim 5 wherein said pits in said substrate comprise chemically produced etch pits.

9. An acoustic transducer as claimed in claim 1 wherein said dielectric film is selected from an electric film and piezoelectric polymer film.

10. An acoustic transducer as claimed in claim 9 wherein said dielectric film is a polyimide film.

11. An acoustic transducer as claimed in claim 1 wherein said pits extend through said substrate.

12. An acoustic transducer as claimed in claim 3 wherein said metallic film is selected from gold and aluminum.

13. An acoustic transducer as claimed in claim 7 wherein said pits are hexagonal and have an average depth of up to about 30 μm.

14. A method for producing an acoustic transducer operable in air up to at least 2 MHz, comprising:
   (a) producing a selected pattern of pits in a surface of a conducting substrate;
   (b) superimposing said pitted surface with a film of dielectric material so as to trap air into a plurality of said pits; and
   (c) superimposing a conducting electrode over said dielectric film.

15. A method as claimed in claim 14, wherein said pits are produced by chemical etching, ion beam milling or reactive ion etching.

16. A method as claimed in claim 14 wherein said conducting substrate is a semi conductor material selected from silicon and doped silicon.

17. A method as claimed in claim 16 wherein said pits are up to 30 μm deep.

18. A method as claimed in claim 14 including the step of spin coating a polyimide material on said substrate so as to form said film of dielectric material.

19. A method as claimed in claim 18 wherein said polyimide is Probimide 200.

20. A method as claimed in claim 14 wherein said planar conducting electrode comprises a metallic layer selected from aluminum and gold.

21. A method as claimed in claim 20 wherein said metallic layer is applied by vapour phase deposition.

22. An acoustic transducer operable in air up to at least 2 MHz, comprising a substrate having at least one conducting surface;
   at least one dielectric film having a plurality of pits of selected size and shape distributed thereover in a selected pattern, superimposed over said substrate so as to provide a plurality of air pockets between said dielectric film; and
   a conducting upper electrode superimposed on said dielectric film.

23. An acoustic transducer as claimed in claim 22 wherein said pits extend through said dielectric film.

* * * * *